United States Patent [19]

Price et al.

[11] 4,421,424

[45] Dec. 20, 1983

[54] INSTRUMENT AND METHOD FOR CONTROL TESTING OF VULCANIZED RUBBER

[75] Inventors: Keith Price, Rixensart, Belgium; Michael Mathews, Swindon, England

[73] Assignee: Monsanto Europe S.A.

[21] Appl. No.: 341,391

[22] Filed: Jan. 21, 1982

[30] Foreign Application Priority Data

Jan. 29, 1981 [GB] United Kingdom ............... 8102774

[51] Int. Cl.³ ............................................. G01N 3/32
[52] U.S. Cl. ........................................ 374/48; 374/53
[58] Field of Search ................ 73/843, 847; 374/48, 374/53

[56] References Cited

U.S. PATENT DOCUMENTS 3,531,996  10/1970  Harris et al. ........................ 374/48
3,686,933   8/1972  Sokolov et al. ..................... 73/101

FOREIGN PATENT DOCUMENTS 1036904  7/1966  United Kingdom .
1126995  9/1968  United Kingdom .
1247371  9/1971  United Kingdom .

*Primary Examiner*—Herbert Goldstein
*Attorney, Agent, or Firm*—Gordon B. Seward

[57] ABSTRACT

A curemeter has dies maintainable at a substantially uniform vulcanization temperature, the dies being arranged to be separable and for closure, and which when closed define a cavity for accommodating a sample of compounded rubber, means for subjecting the sample of compounded rubber to oscillating shear strain and means for obtaining a signal derived from such oscillation and correlating with the degree of vulcanization of the sample. The curemeter of the invention is characterized by also having separable dies maintainable at the same substantially uniform vulcanization temperature as the first said dies, and which when closed define at least one cavity for accommodating a further sample of the compounded rubber for vulcanization under static conditions.

5 Claims, 3 Drawing Figures

INSTRUMENT AND METHOD FOR CONTROL TESTING OF VULCANIZED RUBBER

This invention relates to a method and apparatus for the preparation of test specimens of vulcanized rubber.

Curemeters, which measure changes in the stiffness of samples of rubber undergoing vulcanization, have been used for many years in the batch control testing of mixed rubber.

One such curemeter is that described in British Patent Specification No. 1,036,904 where the sample of rubber is held in a closed chamber containing a rotor to which an angular oscillatory motion of constant amplitude is applied, and the progress of vulcanization is followed by monitoring the torque required to effect the angular oscillatory motion. The use of this type of curemeter is specified in ASTM Standard Test Method D2084-79, British Standard Test Method 1673 Part 10 and ISO 3417 1977.

In other curemeters, a chamber to accommodate a sample of rubber undergoing vulcanization is formed between two plate members, one of which is adapted for angular oscillatory motion relative to the other, and the progress of vulcanization is followed by monitoring either the torque required to effect constant angular displacement of the first plate member or the stress tranmitted to the second plate member by such angular oscillatory motion (See, e.g., British Pat. Nos. 1,126,995 and 1,247,371).

Such curemeters give useful information on whether the batch of rubber sampled in the curemeter is within specification in respect of many features of its composition, behavior and properties. However, for certain applications, it is critical that the vulcanized rubber should be within specification in respect of properties such as density, hardness, resilience or tensile strength, which are not measured by a curemeter. Hitherto, the preparation of test specimens on which to measure such properties had involved a separate curing operation, sometimes in presses holding samples from several different batches, so that the samples require careful identification. Moreover, such preparation is a manpower- and energy-consuming process, and there is usually considerable uncertainty on how closely matched are the conditions under which such separately prepared samples are vulcanized, to the conditions of vulcanization of the sample in the curemeter.

BRIEF SUMMARY OF THE INVENTION

The present invention provides a means of avoiding the shortcomings of the previous practice. In one aspect, the invention concerns a method of preparing a test specimen of vulcanized rubber for use in determining physical properties of the specimen, which comprises (a) heating a sample of compounded rubber in a test-specimen mold cavity maintained at a substantially uniform vulcanization temperature while, beginning at substantially the same time, a further sample of the same compounded rubber is heated at substantially the same vulcanization temperature in a cavity in which the said further sample is subjected to shearing strain imparted by mechanical oscillation, and a signal derived from such oscillation correlating with the degree of vulcanization of the further sample is obtained, and (b) removing the test specimen from its mold cavity at a time corresponding to a desired degree of vulcanization as indicated by the said signal.

In another aspect, the invention relates to a curemeter having dies maintainable at a substantially uniform vulcanization temperature, the said dies being arranged for separation and closure, and which when closed define a cavity for accommodating a sample of compounded rubber, means for subjecting the sample of compounded rubber to oscillating shear strain and means for obtaining a signal derived from such oscillation and correlating with the degree of vulcanization of the sample, characterized in that the apparatus also includes separable dies maintainable at the same substantially uniform vulcanization temperature as the first said dies, and which when closed define at least one cavity for accommodating a further sample of the compounded rubber for vulcanization under static conditions.

Normally a cavity is formed by the closure of two dies. Each die of a pair may be shaped the same, or, for example, one may comprise a face and said walls design to mold one face and the edge respectively of a flat specimen while the second die provides simply a plane surface which molds the other face of the specimen.

In curemeters in which a chamber to accommodate a sample of rubber undergoing vulcanization is formed between two plate members, one of which is adapted for angular oscillatory motion relative to the other, the two plate members are to be regarded as dies for the purposes of the present invention.

DETAILED DESCRIPTION

Preferred curemeters of the invention include means for effecting the substantially simultaneous closure of the dies forming the cavity in which the sample of rubber is subjected to oscillating shear strain and each set of dies forming a cavity in which a further sample of rubber is vulcanized under static conditions.

This result can be achieved, in the usual case where a cavity is formed by the closure of two dies, by an arrangement in which one die of each cavity-forming pair is fixed to a carrier adapted through guide means for controlled travel towards and away from a base on which the other die of each cavity-forming pair is mounted. Accurate mating of the two dies of each pair can also thereby be ensured.

The dies may be directly heated and maintained at a substantially uniform temperature by means of temperature controllers. In a preferred arrangement, however, the carrier and base referred to above are heatable platens with which the dies are in efficient thermal contact and which have thermal capacities which are large relative to those of the dies.

A further preferred feature is that the volumes of all the cavities are the same within ±25%, preferably within ±10%. By this means, the rate of heating and the attainment of thermal equilibrium is substantially the same for each sample.

Figure 1:
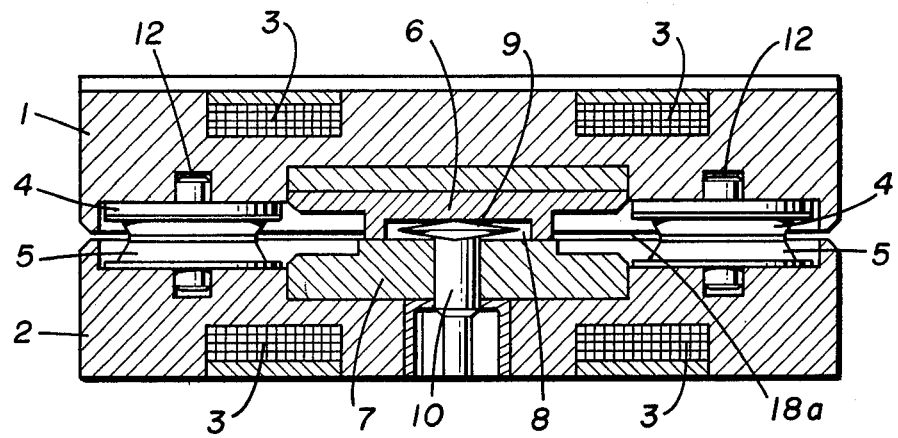
FIG. 1 is a side elevation, in partial section, of a curemeter platen and die assembly according to the invention.

The assembly of FIG. 1 comprises an upper platen 1 and a lower platen 2, the said assembly being suitable for use in a curemeter of the type described in British Pat. No. 1,036,904.

The platens include heater elements 3 and various dies inset into the adjacent faces of the platens. Dies 4 and 5 together form a mold for the static vulcanization of a sample of compounded rubber to produce a specimen of the vulcanizate for subsequent use in physical tests such as density, hardness or resilience. Dies 6 and 7 enclose a chamber 8 containing a bi-conical rotor 9. This rotor is fastened to the end of a shaft 10 journalled in the base of die 7, and is adapted to transmit from means not shown (but see, for example, FIG. 1 of British Pat. No. 1,036,904) an oscillating shear strain to a sample of rubber undergoing vulcanization in chamber 8. The manner in which information on the progress of the vulcanization of the sample can be derived from such apparatus is described in British Pat. No. 1,036,904.

Figure 2:
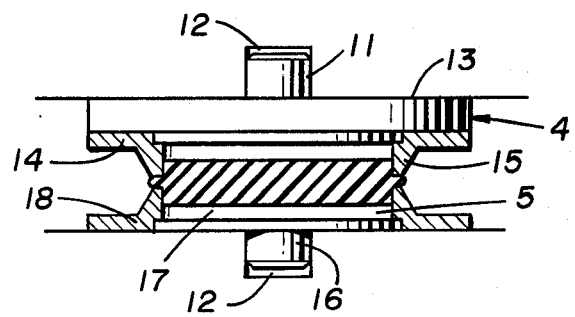
FIG. 2 is a side section of a die for a disc-shaped specimen.

FIG. 2 shows an enlarged cross-sectional view of one set of dies 4 and 5. Die 4 comprises a stud 11 (which locates in a corresponding socket 12 in the platen 1) coaxial with a circular plate 13 having upper and lower portions of relatively greater and smaller diameters respectively. Plate 13 is preferably made from metal having high thermal conductivity, for example aluminum. A collar, 14, preferably made from metal having good durability, for example tool steel, is shaped to surround the periphery of the smaller diameter portion of plate 13 and to abut against the outer annular underside of the larger diameter portion. The part of the collar 14 which surrounds the periphery of the smaller diameter portion of plate 13 has a tapered section 15 which extends beyond the horizontal lower face of the plate 13, thus forming a side wall of the mold.

The construction of die 5 is similar, comprising stud 16, plate 17 and collar 18.

To prepare specimens of vulcanized rubber, platens 1 and 2 are separated, and samples of the rubber mix under test are placed in each of dies 5, the volume of each sample being slightly more than that required to fill completely the mold formed when dies 4 and 5 are brought together. A sample of the same rubber mix is also placed on rotor 9, its volume being slightly more than the volume of the chamber 8 less the volume of rotor 9.

Platens 1 and 2 are then brought together, the slight excess volume of rubber placed in each of the die cavities being extruded during the final stages of closure into the small gap 18a between platens 1 and 2. The tapered sections of collars 14 and 18 remain separated by a thin section of rubber pinched between them. However, this thin section cures more quickly than the mass of the sample to form an integral seal round the die, so that an adequate pressure is maintained within the mold to form a good non-porous specimen.

When the curemeter is in operation for the routine testing of rubber samples, the platens are normally kept throughout at vulcanization temperature, so that after closure, the samples in the die cavities are rapidly heated to the required vulcanization temperature. Oscillation of the rotor and monitoring of the progress of vulcanization of the sample in chamber 8 are commenced and are continued until the desired degree of vulcanization (for example that corresponding to maximum modulus) of the rubber is reached.

The dies are then opened by separating platens 1 and 2 and the specimens removed from dies 4 and 5.

Figure 3:
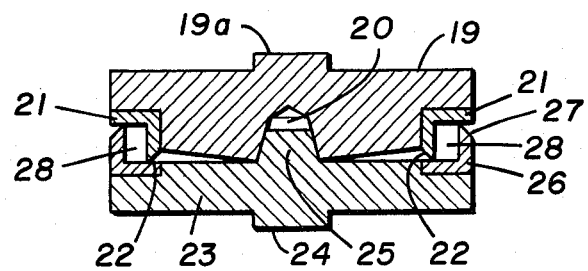
FIG. 3 is a side section of a die for a ring-shaped specimen.

The die assembly shown in FIG. 3 comprises an upper plate 19 having a stud 19a for locating the plate on a platen in a manner analogous to the location of die 4 on platen 1 in FIG. 1. An axial socket 20 is formed in the lower face of plate 19, the face itself being angled slightly upwards from the rim of the socket towards the periphery of the plate. A flanged ring 21, suitable made of tool steel, is located in a step in the periphery of the plate. The depth of the cylindrical part of the ring is greater than the thickness of the plate at its rim which the cylindrical part of the ring encircles, and the protruding end is sharpened to a knife edge at 22.

The lower plate 23 is formed with a stud 24 and an axial spigot 25 which mates with the socket 20 of plate 19, thus ensuring that during closure, the upper and lower dies remain concentric. The horizontally disposed part of a second flanged ring 26 is inset and secured into the periphery of the upper face of plate 23, forming a surface for cooperation with the knife edge 22. The upper rim of the cylindrical part of ring 26 is sharpened to a knife edge 27 which bears against the undersurface of the horizontal part of ring 21.

A specimen is formed by opening the dies and placing a sample of rubber mix over the spigot 25. On closure of the dies, the rubber is forced outwards towards the peripheries of the plates and eventually fills the annular space 28 between rings 21 and 26 where it is vulcanized to give a ring-shaped specimen.

Cure curves obtained in tests carried out with a platen and die assembly as described with references to FIGS. 1 and 2, dies 4 and 5 having dimensions giving a molded disc-shaped specimen 35–45 mm in diameter and 4–6.5 mm in thickness, were substantially identical with those obtained on samples of the same rubber mix using a curemeter having only the rotor-containing die cavity required by the Standard methods referred to above.

We claim:

1. Apparatus comprising a curemeter having first dies maintainable at a substantially uniform vulcanization temperature, the said first dies being arranged to be separable and for closure, and which when closed define a cavity for accommodating a sample of compounded rubber, means for subjecting the sample of compounded rubber to oscillating shear strain and means for obtaining a signal derived from such oscillation and correlating with the degree of vulcanization of the sample characterized in that the apparatus also includes other separable dies maintainable at the same substantially uniform vulcanization temperature as the first said dies, which other separable dies when closed define at least one cavity for accommodating a further sample of the compounded rubber for vulcanization under static conditions, the apparatus further including means for effecting the substantially simultaneous closure of the first dies forming the cavity in which the sample of rubber is subjected to oscillating shear strain and of each set of the other dies forming a cavity in which a further sample of rubber is vulcanized under static conditions.

2. A curemeter according to claim 1 wherein each cavity is formed by the closure of two dies, one die of each cavity-forming pair being fixed to a carrier adapted through guide means for controlled travel towards and away from a base on which the other die of each cavity-forming pair is mounted.

3. A curemeter according to claim 2 wherein the carrier and base are heatable platens with which the dies are in efficient thermal contact, the platens having thermal capacities larger than those of the dies, and wherein the cavity in which the sample of rubber is subjected to oscillating shear strain is a closed chamber containing a rotor to which an angular oscillating motion can be applied.

4. A curemeter according to the claim 1 wherein the volume of each cavity for accommodating a sample of rubber for vulcanization under static conditions is the same within ±25% as the volume of the cavity for accommodating the sample of rubber which is to be subjected to oscillating shear strain.

5. A method of preparing a test specimen of vulcanized rubber for use in determining physical properties of the specimen, which comprises (a) heating a sample of compounded rubber in a test-specimen mold cavity maintained at a substantially uniform vulcanization temperature while, beginning at substantially the same time, a further sample of the same compounded rubber is heated at substantially the same substantially uniform vulcanization temperature in a cavity in which the said further sample is subjected to shearing strain imparted by mechanical oscillation, and a signal derived from such oscillation correlating with the degree of vulcanization of the further sampled is obtained, and (b) removing the test specimen from its mold cavity at a time corresponding to a desired degree of vulcanization as indicated by the said signal.

* * * * *